United States Patent [19]

Baffelli et al.

[11] Patent Number: 5,266,304
[45] Date of Patent: Nov. 30, 1993

[54] WATER-FREE PROPHYLECTIC PASTE CONTAINING PERLITE

[75] Inventors: Gianni Baffelli, Tesserete; Beat A. von Weissenfluh, Gentilino, both of Switzerland

[73] Assignee: Hawe-Neos Dental, Switzerland

[21] Appl. No.: 927,832

[22] Filed: Aug. 10, 1992

[30] Foreign Application Priority Data

Aug. 19, 1991 [CH] Switzerland ............... 02437/91

[51] Int. Cl.$^5$ ............... A61K 7/16; A61K 7/18
[52] U.S. Cl. ............... 424/49; 51/308; 51/311; 252/99; 424/52
[58] Field of Search ............... 424/49-58

[56] References Cited

U.S. PATENT DOCUMENTS

| | | | |
|---|---|---|---|
| 2,059,396 | 11/1936 | Ripert | 424/49 |
| 3,228,845 | 1/1966 | Najjar | 424/49 |
| 3,689,637 | 9/1972 | Pader | 424/52 |
| 3,705,940 | 12/1972 | Kirchgassner et al. | 424/49 |
| 3,868,336 | 2/1975 | Mazzola | 252/135 |
| 3,978,205 | 8/1976 | Newman et al. | 424/49 |
| 4,051,056 | 9/1977 | Hartmann | 252/99 |
| 4,132,771 | 1/1979 | Schreiber et al. | 424/52 |
| 4,143,126 | 3/1979 | Gappar | 424/49 |
| 4,159,316 | 6/1979 | Januszewski et al. | 424/49 |
| 4,187,287 | 2/1980 | Schreiber et al. | 424/49 |
| 4,294,894 | 10/1981 | Vellucci | 424/49 |
| 4,485,089 | 11/1984 | Leipold | 424/49 |
| 4,526,701 | 7/1985 | Rubin | 252/113 |
| 5,094,771 | 3/1992 | Ahmed | 252/99 |
| 5,124,143 | 6/1992 | Muhlemann et al. | 424/49 |

FOREIGN PATENT DOCUMENTS

| | | |
|---|---|---|
| 406912 | 12/1934 | Belgium . |
| 206349 | 10/1983 | Czechoslovakia . |
| 0268763 | 9/1987 | European Pat. Off. . |
| 2204903 | 3/1973 | Fed. Rep. of Germany . |
| 2747852 | 5/1979 | Fed. Rep. of Germany . |
| 2158217 | 6/1973 | France . |
| 2173996 | 10/1973 | France . |
| 61-118499 | 6/1986 | Japan . |
| 250356 | 2/1970 | U.S.S.R. . |
| 2178441 | 2/1987 | United Kingdom . |

OTHER PUBLICATIONS

Lutz et al Quintessence Int. 24(1):53-63 (1993) "Self-Adjusting Abrasiveness:Prophylaxis Pastes".
Putt et al J. Dent. Res. 58(7): 1659-1663 (1979) "Prophylaxis Pastes of Sodium Potassium Aluminum Silicate and Fluoride".
Barbakow et al Quintessence Int. 18:29-34 (1987) "Relative Dentin Abrasion by Dentifrices and Prophylaxis Pastes".
Roulet et al J. Periodontol 53:257-266 (1982) "Surface Roughness . . . After Polishing with Prophylaxis and Polishing Pastes".
Zampa et al J. Periodontol. 43: 125-126 (1992) "Effect of Polishing Agents on Root Roughness".
Stookey J. Dent. Res. 57:36 (1975) "In Vitro Estimates of Enamel and Dentin Abrasion Associated with a Prophylaxis".
Putt et al J. Dent. Res. 54:527-534 (1975) "Physical Characteristics of a New Cleaning and Polishing Agent for Use in a Prophylaxis Paste".
Mellberg Clin. Prev. Dent 6:13-18 (1979) "Relative Abrasivity of Dental Prophylactic Pastes and Abrasives on Enamel and Dentin".

Primary Examiner—Shep K. Rose
Attorney, Agent, or Firm—Ostrolenk, Faber, Gerb & Soffen

[57] ABSTRACT

The dental care and cleaning composition is a water-free paste containing at least 40% by weight of perlite as a sole and combined cleaning and polishing body, a stabilizer for the perlite in the sense of a controlled particle disintegration during use, a wettening agent for the perlite and at least 40% by weight of propylene glycol The use for the cleaning of teeth yields successively a cleaning and a polishing effect.

13 Claims, No Drawings

WATER-FREE PROPHYLECTIC PASTE CONTAINING PERLITE

The present invention is related to a dental care or tooth cleaning composition in paste form for the cleaning of teeth. It particularly concerns a composition for prophylactic dental hygienics.

It is already known that the formation and the progress of caries is linked to the more or less hard, solidly adhering dental tartar, which forms in spite of daily tooth cleaning. This tartar should be removed at least three times a year in order to avoid or at least drastically reduce the formation of caries. During this cleaning, a paste which contains abrasive bodies is distributed on the tooth surface under pressure by means of a very rapidly rotating rubber disk or circular brush, and a cleaning effect is obtained by forming a cleaning and polishing film between the rotating tool and the tooth surface.

However, the relatively frequent application of said tooth cleaning composition leads, besides the removal of the dental tartar, to an erosion of the hard dental enamel, which should be kept as low as possible. The abrasiveness is measured on extracted and radioactively treated human teeth by measuring the increase of the radioactivity of a suspension of the tooth cleaning composition to be assayed after the treatment of the test teeth. The treatment of dental dentine gives the so-called RDA value, and the treatment of dental enamel supplies the REA value (Journal of Dental Research 55(4), 1976, p. 563). A first orientation regarding abrasion is obtained by the treatment of copper plates and the determination of the copper loss.

From French published patent applications no. FR-A-2,158,217 and FR-A-2,173,996, aqueous products are known for the cleaning and the protection of teeth, and these products are suspensions or pastes. According to FR-A-2,158,217, the products contain abrasive agents, polishing agents and thickening agents, and the abrasive agents comprise finely divided silicates, particularly aluminum silicate of a defined composition and having a particle size comprised between 5 and 15 μm or from 10 to 30 μm. As polishing agents, precipitated silicic acid is used, and the thickening agent is fumed silica ("AEROSIL"). The aluminum silicates are not further described, and it remains unclear how they are obtained. French patent application FR-A-2,173,996 discloses a transparent tooth paste comprising precipitated silicic acid as a polishing and optionally also as an abrasive agent.

Finally, European patent application no. EP-A2-0,268,763 discloses a dental cleaning composition wherein the cleaning body is a mixture of synthetic precipitated silica and perlite. These compositions contain aqueous glycerol as a liquid phase. Three pastes are provided for the treatment of the teeth by the dental hygienist, and these composition must be applied one after the other and must contain different particle sizes.

It is a first and major object of this invention to provide a pasty dental care composition for prophylactic dental hygienics and for the cleaning and polishing of dental surfaces which has been fundamentally improved over the known compositions. A further object of the invention is to provide such a cleaning composition having an outstanding cleaning power while simultaneously taking better care of the dental surfaces and giving a better prophylaxis. Still another object of the invention is to provide such compositions which can be handled better than the known compositions. In particular, the new compositions should be formulated as a stable dispersion of cleaning bodies.

The dental cleaning composition of this invention which meets the objects defined above contains as a sole and combined cleaning and polishing body, a finely divided rock having sharp-edged particles which disintegrate into smaller but also sharp-edged particles under the conditions of use of the dental care composition. The composition of the invention furthermore contains 1,2-propanediol and at least one wetting agent for the rock particles. It is important that the composition is substantially free from water.

The different features of the composition of the invention will now be discussed and, when desired or necessary, be compared with the properties of analogous known dental care or cleaning compositions.

The tooth cleaning paste of the invention contains, as a sole and combined cleaning and polishing body, fine particles of certain rocks, particularly perlite, in amounts of preferably at least 40% by weight. In the frame of this invention, the properties and the behavior of perlite have been extensively investigated. Perlite is a rhyolitic vitreous rock of volcanic origin having the following composition according to elemental analysis, the variations being due to different origins:

| | |
|---|---|
| 72.1 to 74.2% | $SiO_2$ |
| 12.3 to 13.5% | $Al_2O_3$ |
| 0.5 to 1.8% | $Fe_2O_3$ |
| up to 0.1% | $TiO_2$ |
| 0.45 to 1.5% | $CaO$ |
| 0.03 to 0.5% | $MgO$ |
| 3.0 to 4.6% | $Na_2O$ |
| 3.8 to 5.0% | $K_2O$ and |
| 2.8 to 4.0% | water |

Perlite is thus substantially a sodium potassium aluminum silicate. The particles which are obtained by grinding show the property of exploding on heating due their water content. In the present document, exclusively the exploded (expanded) perlite is discussed and used. Perlite shows, like the other mentioned rocks, i.e. ignimbrite, tuff, trass, etc., an internal cell structure, and the fragments remaining after grinding and sieving resemble broken egg shells under the microscope, i.e. sharp-edged and mostly curved shell-like bodies. If these bodies are further broken, a diminished fraction is obtained wherein the edges of the particles are also sharp, and this property is conserved until the finest powder.

Until now, at least two pastes had to be used for tooth care, namely a cleaning paste comprising cleaning bodies, and a polishing paste comprising polishing bodies, and these cleaning and polishing bodies were required to show different particle sizes and different other properties in order to fulfill the different functions. The combination of cleaning and polishing bodies in one sole paste, as proposed by FR-A-2,158,217, is useless, since such a combined paste cannot give a finely polished dental surface.

It has now been found in a highly surprising manner that the said finely divided bodies in the dental cleaning and care composition of the invention fulfill both tasks subsequently. The original, relatively coarse particles show a cleaning effect, and they are disintegrated during the cleaning work into finer and finer particles which then have the desired polishing action until the finest polishing. In this manner, an "intelligently dynamic" cleaning and polishing action is obtained, and a desired more or less severe cleaning action can be obtained by simple appropriate selection of the starting particle size of the rock in the cleaning paste.

Another important property of the dental care and cleaning compositions of the invention is the stabilizing of the crystal form of the rocks and of the paste itself. Since such rocks are extremely hydrophobic, an unstabilized paste would rapidly decompose during the cleaning work in the saliva-wet oral cavity. The features of stabilizing will be discussed below.

An important and outstanding embodiment of the invention is a dental care and cleaning composition containing at least 40% by weight, preferably 40 to 50% by weight, of perlite. The compositions according to EP-A-0-268,763 comprise not more than 22% by weight of perlite. In said document, it is stated that perlite has nearly no adsorption ability (under the conditions of the pastes described therein), and there is instability when the proportion of perlite to precipitated silica of 1:1 is shifted to the side of perlite. It has been found that more than 20% by weight of perlite will not be wetted by glycerol. The invention starts from this statement and realizes the feature of the high perlite content within an absolute dispersion by special provisions. As it has been mentioned above, it was one of the aims of the invention to provide an absolutely stable paste having rock particles in relatively very high amounts dispersed therein.

As a result of extensive investigations, it has firstly been found that the presence of water in the cleaning composition must be avoided when particles of the mentioned rocks are used as a sole and combined cleaning and polishing body. It is very difficult to wet such particles, and tremendous amounts of surface active agents would be necessary which would alter the dental care and cleaning composition in an undesired manner. At the same time, it has been found that the intelligently dynamic cleaning action mentioned above can only be achieved with wetted particles; unwetted particles disintegrate immediately into powder under the action of pressure and can thus not act as a cleaning agent.

It has further been found that 1,2-propanediol is particularly appropriate as a non-aqueous solvent and dispersing agent. Although FR-A-2,173,996 already mentions propylene glycol as a component, it is used only in the absence of perlite and only as an addition of about 10% to glycerol which further contains about 15% of water. According to the invention propylene glycol is used in a substantially water-free form, and no water or other solvent is added to the present compositions. In these compositions, the proportion of the propylene glycol is preferably between 40 and 45% by weight. The wetting of the perlite by propylene glycol is achieved by the addition of at least one dispersing agent which displays its effectivity in a water-free phase and which thus guarantees the wetting of the hydrophobic perlite surfaces. It is preferred to use a dioctyl sulfosuccinate whose proportion in the compositions of the invention is generally from about 1 to 3% by weight. The product "REWOPOL SBDO 70", which has particularly been used, has further, a desired effect against plaque and bacteria (U.S. Pat. Nos. 4,375,461; 4,460,564; 4,473,547).

The crystal structure of the rock particles, e.g. of the perlite, should be stabilized. As a stabilizer, the addition of hydrophobic silicic acid has been found to be particularly appropriate, for example of precipitated silicic acid, particularly of hydrophobic fumed silica, in an amount of from about 2 to about 5% by weight. An example for this fumed silica is "AEROSIL R 974" of the company DEGUSSA, Germany. This substance confers the paste the desired thixotropy in the anhydrous medium. This finding was highly surprising; the pastes containing this additive behave nearly like solids and can only be liquefied by vigorous shaking. This property is important to give a strong adherence of the paste to the cleaning tool, namely a rotating rubber disk or a brush.

As to the wetting of the Aerosil, the same conditions apply as for the perlite. The wetting and the stability of the paste is improved by the addition of a wetting controlling agent, for example a nonionic product. The product "SILWET L 7600", a polyoxyethylene dimethyl siloxane, only known as a defoamer in aqueous phase, has been found to be particularly appropriate in amounts of from about 0.5 to 1% by weight. Other polyoxyalkylene derivatives are also useful.

Finally, it is advantageous to control the viscosity of the dental care and cleaning composition of the invention in function of its use, i.e. to raise its viscosity. This purpose is achieved by the addition of a thickening and gelating agent soluble in the propylene glycol; examples are cellulosic derivatives such as hydroxypropyl cellulose ("KLUCEL HF") in amounts of from about 0.4 to 0.5% by weight.

All indications referring to percentages and parts given above and below are related to the total weight of the final dental care and cleaning composition. When the stabilizing of the perlite and of the paste and the control of the dynamic disintegration of the rock particles is referred to, it is assumed that several components of the composition yield a combined synergistic effect.

Preferred dental care and cleaning compositions according to the invention are generally composed in the following ranges:

| Perlite, average particle size 20 to 40 μm, | 40 to 45% |
| --- | --- |
| Propylene glycol | 40 to 45% |
| "KLUCEL HF" | 0.4 to 0.5% |
| "AEROSIL R 974" | 2 to 5% |
| "REWOPOL SBDO 70" | 1 to 3% |
| "SILWET L 7600" | 0.5 to 1% | and additionally, as far as desired, pigments, sweetening agents, fluorine compounds, and aromatic oils and flavoring agents.

The abrasive properties of the cleaning and polishing agents defined above are the following:

REA value: 4.4
RDA value: 24

The abrasion values are thus much smaller than those of known pastes.

The dental care and cleaning compositions according to this invention can be obtained by appropriate mixing of the components; the rock particles are first comminuted to the desired starting size and sieved accordingly.

It has been found that the compositions of the invention allow the cleaning and the polishing of a tooth in only about 10 s. The surface of the enamel and of the dentine is absolutely free from corrugations, striations and scratches.

Modifications and improvements of the dental care and cleaning compositions of the invention can be operated by the knowledge of the man skilled in the art within the scope defined in the patent claims. This refers particularly to the kind and provenience of the used rocks as well as to their preliminary treatment and to the selection of the remaining additives from the multitude of commercial products. Furthermore, the relative proportions of the individual components depend on their nature; e.g. other rocks than perlite may require other amounts and kinds of the remaining components.

We claim:

1. A dental care and cleaning composition in prophylactic paste form for the cleaning and polishing of dental surfaces, characterized by the fact that it contains, as a sole and combined cleaning and polishing body at least about 40% by weight of perlite as, a finely divided rock having sharp-edged particles which disintegrate into smaller but also sharp-edged particles under the conditions of use of the dental care composition, furthermore propylene glycol, or 1,2-propanediol and at least one wetting agent for the perlite particles, said composition being substantially free from water.

2. The composition of claim 1, wherein the perlite has an average particle size comprised between about 20 and 40 μm.

3. The composition of claim 1, comprising at least about 40% by weight of propylene glycol, furthermore said wetting agent and at least one stabilizer for the combined cleaning and polishing body.

4. The composition of claim 3, wherein the stabilizer comprises a hydrophobic, finely divided silicic acid in amounts of from about 2 to about 4% by weight giving thixotropy to the composition.

5. The composition of claim 3, wherein the wetting agent comprises a dialkylsulfosuccinate.

6. The composition of claim 3, further comprising another wetting agent, namely a polyoxyalkylene dimethyl siloxane.

7. The composition of claim 1, further comprising at least one hydroxyalkyl cellulose which is soluble in the propylene glycol under gel formation.

8. The composition of claim 3, further comprising pigments, fluorine compounds, sweetening agents flavoring agents and mixtures thereof.

9. The composition of claim 3 claims, having a composition in the following range, in percent by weight:

| | |
|---|---|
| Perlite, average particle size 20 to 40 μm, | 40 to 45 |
| Propylene glycol | 40 to 45 |
| Hydroxypropyl cellulose | 0.4 to 0.5 |
| Fumed silica | 2 to 5 |
| Dioctylsulfosuccinate | 1 to 3 |
| Polyoxyethylene dimethylsiloxane | 0.5 to 1 |
| Sweetening agent, pigment, flavoring agent, fluorine source, bactericidal agent | q.s. |

10. The composition of claim 4, wherein the wetting agent comprises a dialkylsulfosuccinate.

11. The composition of claim 10, further comprising at least one hydroxyalkyl cellulose which is soluble in the propylene glycol under gel formation.

12. The composition of claim 6, wherein the first wetting agent comprises a dialkylsulfosuccinate.

13. The composition of claim 11, wherein the first wetting agent comprises a dialkylsulfosuccinate.

* * * * *